(12) United States Patent
Wang (10) Patent No.: US 12,058,932 B2
(45) Date of Patent: Aug. 6, 2024

(54) CO-HOST MATERIAL, LIGHT EMITTING LAYER COMPOSITION, AND LIGHT EMITTING DEVICE

(71) Applicant: BOE TECHNOLOGY GROUP CO., LTD., Beijing (CN)

(72) Inventor: Siqi Wang, Beijing (CN)

(73) Assignee: BOE TECHNOLOGY GROUP CO., LTD., Beijing (CN)

( * ) Notice: Subject to any disclaimer, the term of this patent is extended or adjusted under 35 U.S.C. 154(b) by 627 days.

(21) Appl. No.: 17/355,351

(22) Filed: Jun. 23, 2021

(65) Prior Publication Data

US 2022/0059776 A1 Feb. 24, 2022

(30) Foreign Application Priority Data

Aug. 21, 2020 (CN) .......................... 202010848940.1

(51) Int. Cl.
| | | |
|---|---|---|
| H01L 51/50 | (2006.01) | |
| C07D 209/86 | (2006.01) | |
| C07D 239/26 | (2006.01) | |
| C07D 251/24 | (2006.01) | |
| C07F 7/08 | (2006.01) | |
| C09K 11/06 | (2006.01) | |
| H10K 85/40 | (2023.01) | |
| H10K 85/60 | (2023.01) | |
| H10K 50/11 | (2023.01) | |
| H10K 101/00 | (2023.01) | |

(Continued)

(52) U.S. Cl.
CPC ....... H10K 85/6572 (2023.02); C07D 209/86 (2013.01); C07D 239/26 (2013.01); C07D 251/24 (2013.01); C07F 7/0812 (2013.01); C09K 11/06 (2013.01); H10K 85/40 (2023.02); H10K 85/654 (2023.02); C09K 2211/1018 (2013.01); H10K 50/11 (2023.02); H10K 2101/30 (2023.02); H10K 2101/90 (2023.02); H10K 2102/351 (2023.02)

(58) Field of Classification Search
None
See application file for complete search history.

(56) References Cited

U.S. PATENT DOCUMENTS

| | | | |
|---|---|---|---|
| 2020/0203651 A1 | 6/2020 | KunShan | |
| 2020/0203652 A1 | 6/2020 | KunShan | |

FOREIGN PATENT DOCUMENTS

| | | |
|---|---|---|
| CN | 101096357 A | 1/2008 |
| CN | 109192874 A | 1/2019 |
| CN | 109411634 A | 3/2019 |

OTHER PUBLICATIONS

China Patent Office, First Office Action dated Mar. 2, 2022, for corresponding Chinese application 202010848940.1.

(Continued)

*Primary Examiner* — Gregory D Clark
(74) *Attorney, Agent, or Firm* — HOUTTEMAN LAW LLC (57) ABSTRACT

The present disclosure provides a co-host material, a composition for forming a light emitting layer, and a light emitting device. The co-host material can at least partially solve the difficulty in the limited selection of thermally activated delayed fluorescent materials in the existing light emitting devices, and the difficulty in providing a light emitting layer of a blue light emitting device. The co-host material comprises a first compound and a second compound each having a specific general formula.

20 Claims, 4 Drawing Sheets

(51) Int. Cl.
*H10K 101/30* (2023.01)
*H10K 102/00* (2023.01)

(56) References Cited

OTHER PUBLICATIONS

Yi, et al., "Harnessing a new co-host system and low concentration of New TADF Emitters Equipped with Trifluoromethyl- and Cyano-substituted Benzene as Core for High-Efficiency Blue OLEDs", ACS Applied Materials and Interfaces, pp. 2724-2732, Dec. 17, 2019.

CO-HOST MATERIAL, LIGHT EMITTING LAYER COMPOSITION, AND LIGHT EMITTING DEVICE

TECHNICAL FIELD

The present disclosure relates to the technical field of organic electroluminescence, and particularly relates to a co-host material (a composite host material) capable of being used as a host material of a light emitting layer, a composition for forming the light emitting layer, a light emitting device, a display substrate and a display device, in particular to a co-host material for the light emitting layer and a light emitting layer material in an organic light emitting diode (OLED), as well an OLED light emitting device, an OLED display substrate and an OLED display device.

BACKGROUND ART

In light emitting devices such as an OLED, an exiplex may be used as a host material of a light emitting layer, and a thermally activated delayed fluorescent (TADF) material may be used as a dopant material.

However, use of the exciplex host material limits selection in the thermally activated delayed fluorescent material, and it is difficult to obtain a light emitting layer for a blue light emitting device.

SUMMARY

According to the first aspect of the present disclosure, it provides a co-host material comprising:

a first compound represented by formula I of wherein X is selected from carbon and silicon; each $R_1$ is independently any one selected from a group consisting of hydrogen, carbazole, dibenzocarbazole, dibenzofuran and dibenzothiophene, and at least one of $R_1$ is carbazole connected to the benzene ring through a nitrogen atom in the carbazole; each $R_2$ is independently any one selected from a group consisting of hydrogen, substituted or unsubstituted C1-C12 alkyl, substituted or unsubstituted C6-C30 arylene, and substituted or unsubstituted C3-C30 heteroarylene; and in the case of substitution, at least one hydrogen of the C1-C12 alkyl, the C6-C30 arylene, and the C3-C30 heteroarylene is substituted with at least one selected from the group consisting of halogen atom, hydroxyl group, amino group, aryl group, ester group, thiol group, cyano group, and nitro group, and/or at least one methylene is substituted with at least one selected from the group consisting of oxygen atom, imino group, sulfonyl group, carbonyl group, arylene, —C(=O)O—, sulfur atom, and nitroso group; and a second compound represented by formula II of wherein each Y is independently selected from carbon and nitrogen, and at least one Y is nitrogen; each Ar is independently selected from C6-C30 arylene and a single bond, wherein the single bond means that R is directly connected to the benzene ring through the single bond; each R is independently any one selected from the group consisting of halogen, halogen-substituted C1-C6 alkyl, sulfonyl group, carbonyl group, thiol group, cyano group and nitro group, and at least one of R is halogen or halogen-substituted C1-C6 alkyl, wherein C6-C30 arylene is optionally substituted by at least one selected from the group consisting of halogen atom, halogen-substituted C1-C6 alkyl, hydroxyl group, amino group, aryl group, ester group, thiol group, cyano group and nitro group.

Optionally, at least one of Ar is phenyl or naphthyl, and at least one R is trifluoromethyl or cyano group.

Optionally, each $R_2$ is independently selected from H and C1-C4 alkyl.

Optionally, the co-host material satisfies energy level relationship of:

$|HOMO_1 - HOMO_2| > 0.3$ eV;

$|LUMO_1 - LUMO_2| > 0.2$ eV;

$|HOMO_1 - LUMO_2| > 3.5$ eV, or $|HOMO_2 - LUMO_1| > 3.5$ eV;

$\Delta Est > 0.3$ eV;

$T_{11} > 2.65$ eV, and $T_{12} > 2.65$ eV;

wherein, | | represents an absolute value, $HOMO_1$ is the highest occupied molecular orbital level of the first compound, $HOMO_2$ is the highest occupied molecular orbital level of the second compound, $LUMO_1$ is the lowest unoccupied molecular orbital level of the first compound, $LUMO_2$ is the lowest unoccupied molecular orbital level of the second compound, $\Delta Est$ is the difference between the triplet excited state energy and the singlet excited state energy of the co-host material, $T_{11}$ is the triplet excited state energy of the first compound, and $T_{12}$ is the triplet excited state energy of the second compound.

Optionally, in the co-host material, the first compound is present in a mass percentage of 40% to 60%, and the second compound is present in a mass percentage of 40% to 60%.

Optionally, in the co-host material, the first compound is present in a mass percentage of 48% to 52%, and the second compound is present in a mass percentage of 48% to 52%.

Optionally, the first compound is at least one selected from the group consisting of:

,

,

, and

Optionally, the second compound is at least one selected from the group consisting of:

Optionally, the co-host material is not an exciplex.

According to the second aspect of the present disclosure, it provides a composition for forming a light emitting layer, comprising:

the co-host material described above; and a thermally activated delayed fluorescent material doped in the co-host material.

Optionally, in the composition, the thermally activated delayed fluorescent material is present in a mass percentage of 0.5% to 40%; and the co-host material is present in a mass percentage of 60% to 99.5%.

Optionally, in the composition, the thermally activated delayed fluorescent material is present in a mass percentage of 1% to 10%; and the co-host material is present in a mass percentage of 90% to 99%.

Optionally, the thermally activated delayed fluorescent material is at least one selected from the group consisting of a backbone polymeric thermally activated delayed fluorescent polymer, a side chain thermally activated delayed fluorescent polymer, and a dendritic thermally activated delayed fluorescent compound.

Optionally, the thermally activated delayed fluorescent material comprises compounds of:

Optionally, the co-host material is not an exciplex.

According to the third aspect of the present disclosure, it provides a light emitting device, comprising: a light emitting layer formed from the composition described above; and an anode and a cathode disposed on two sides of the light emitting layer respectively.

Optionally, the light emitting device further comprises:

a hole injection layer disposed between the anode and the light emitting layer;

a hole transport layer disposed between the hole injection layer and the light emitting layer;

an electron injection layer disposed between the cathode and the light emitting layer; and an electron transport layer disposed between the electron injection layer and the light emitting layer.

Optionally, the light emitting layer has a thickness of 10 nm to 100 nm.

Optionally, the light emitting device is a red light emitting device, a green light emitting device or a blue light emitting device.

Optionally, the thermally activated delayed fluorescent material comprises compounds of:

According to the fourth aspect, the present disclosure provides a display substrate, comprising:
a base; and
a plurality of light emitting devices disposed on the base, wherein at least a portion of the light emitting devices are any one of the light emitting devices described above.

According to the fifth aspect, the present disclosure further provides a display device comprising:
any one of the display substrates described above.

wherein, the reference numbers are: 1, the light emitting device; 106, the hole injection layer; 105, the hole transport layer; 102, the electron injection layer; 103, the electron transport layer; 104, the light emitting layer; 107, the anode; 108, the cathode; T1, the first transistor; T2, the second transistor; T3, the third transistor; T4, the fourth transistor; T5, the fifth transistor; T6, the sixth transistor; T7, the seventh transistor; 206, the storage capacitor; 201, the first reset terminal; 207, the second reset terminal; 202, the initialized terminal; 203, the gate line terminal; 204, the data line terminal; 208, the control line terminal; 209, the positive electrode terminal; and 205, the negative electrode terminal.

DETAILED DESCRIPTIONS

The present disclosure will be described in detail below with reference to the accompanying drawings and specific embodiments, to enable a skilled person in the art to better understand the technical solutions of the present disclosure.

It should be understood that the specific embodiments and accompanying drawings described herein are given by way of illustration and explanation only, not limitation of the present disclosure.

It should be understood that the various embodiments and features of the embodiments may be combined with each other if there is no conflict.

It should be understood that, for the convenience of description, only the parts related to the present disclosure are shown in the accompanying drawings of the present disclosure, and the parts not related to the present disclosure are not shown in the accompanying drawings.

Definitions

In the present disclosure, the following technical terms should be understood according to the following definitions unless otherwise specified:

A to B means a range of values that includes the value of A, the value of B, and any value greater than A and less than B.

The mass percentage of A in B means A is a part of B, and the mass of A accounts for the relative percentage of B when the total mass of B (including the mass of A) is 100%.

The thermally activated delayed fluorescent (TADF) material may be used in the light emitting layer of OLED. The thermally activated delayed fluorescent material allows a non-radiative triplet excited state to be converted into a radiative singlet state through a reverse intersystem crossing (RISC) process, so that the internal quantum efficiency (IQE) of 100% may be theoretically achieved. In addition, the thermally activated delayed fluorescent material generally does not contain metal, and will not cause pollution, so it has a wide application prospect.

Generally, the thermally activated delayed fluorescent material is mixed as an emitter (dopant material) in the host material of an exciplex to form a light emitting layer of the OLED, which can avoid triplet-triplet annihilation or concentration quenching.

In the above light emitting layer, exciton emission can be caused by the recombination of the bound electron and hole pair (exciton) of the lowest unoccupied molecular orbital (LUMO) level of the acceptor and the highest occupied molecular orbital (HOMO) level of the donor. Therefore, for the organic light emitting diode using the exciplex as the host material, the exciplex may be considered as the host having a small band gap (generally not more than 3 eV); however, this would limit the range of selection for available thermally activated delayed fluorescent dopant materials; meanwhile, since the exciplex does not have a fixed ground state, the ground state potential energy surface of the exciplex rises, and the potential energy surface of the excited state firstly falls and then rises (so that a minimum value exists), thus reducing the radiation energy of the exciplex, and resulting in a red shift of the spectrum. In this case, the actual emission peak of the exciplex is different from the original two peaks, and therefore, it is difficult to use the exciplex as the host material for a light emitting device emitting blue light with a short wavelength.

The present disclosure at least partially solves the problem in terms of the limited selection of thermally activated delayed fluorescent materials in conventional light emitting devices and the difficulty in providing the light emitting layer of the blue light emitting device, and provides a composite material as a host material for light emission, a composition for forming a light emitting layer, a light emitting device, a display substrate, and a display device.

In the first aspect, the present disclosure provides a co-host material for light emission, comprising a first compound and a second compound. In other words, the co-host material of the present disclosure may be formed by mixing the first compound and the second compound. For example, by mixing and co-doping a P-type compound host material and an N-type compound host material, a suitable non-exiplex bipolar composite material is produced with a high T1 (triplet excited energy) and a high S1 (singlet excited energy), which may be combined with TADF emitters as a practical strategy for developing the blue TADF-based OLED.

The host material of the present disclosure refers to the host material used in the light emitting layer of a light emitting device, such as an organic light emitting diode. The host material may be mixed with a dopant material to form the light emitting layer.

In one embodiment, the co-host material of the present disclosure is composed of two substances or compounds, and thus the co-host material is particularly suitable for use with TADF dopant materials.

The first compound may be represented by formula I of wherein X is selected from carbon and silicon; each $R_1$ is independently any one selected from the group consisting of hydrogen, carbazole, dibenzocarbazole, dibenzofuran and dibenzothiophene, and at least one of $R_1$ is carbazole connected to the benzene ring through a nitrogen atom in the carbazole; each $R_2$ is independently any one selected from the group consisting of hydrogen, substituted or unsubstituted C1-C12 alkyl, substituted or unsubstituted C6-C30 arylene, and substituted or unsubstituted C3-C30 heteroarylene; and in the case of substitution, at least one hydrogen of the C1-C12 alkyl, the C6-C30 arylene, and the C3-C30 heteroarylene is substituted with at least one selected from the group consisting of halogen atom, hydroxyl group, amino group, aryl group, ester group, thiol group, cyano group, and nitro group, and/or at least one methylene is substituted with at least one selected from the group consisting of oxygen atom, imino group, sulfonyl group, carbonyl group, arylene, —C(=O)O—, sulfur atom, and nitroso group.

The co-host material according to one embodiment of the present disclosure comprises the first compound represented by the above formula I.

In the formula I, X is carbon (C) or silicon (Si), and when it is silicon, T1 (triplet excited state energy) of the co-host material can be further increased.

The plurality of $R_1$ may be independently selected from the group consisting of hydrogen (H), carbazole, dibenzocarbazole, dibenzofuran, dibenzothiophene and other electron-donating groups, wherein at least one of $R_1$ is carbazole, and the carbazole is connected to the benzene ring of the first compound main portion through a nitrogen atom in the carbazole. When the plurality of $R_1$ in the first compound are all carbazoles, it is not required that all carbazoles are connected to the benzene ring through a nitrogen atom, but a part of carbazoles may be connected to the benzene ring of the first compound main portion through a carbon in the phenyl group and the like.

Each $R_2$ is independently any one selected from the group consisting of hydrogen, substituted or unsubstituted C1-C12 alkyl (the number following the C indicates the number of carbon atoms in the alkyl), substituted or unsubstituted C6-C30 arylene (the number following the C indicates the number of carbon atoms in the arylene), and substituted or unsubstituted C3-C30 heteroarylene (the number following the C indicates the number of carbon atoms in the heteroarylene). In the case of substitution, at least one hydrogen of the C1-C12 alkyl, the C6-C30 arylene, and the C3-C30 heteroarylene is substituted with at least one selected from the group consisting of halogen atom, hydroxyl group, amino group, aryl group, ester group, thiol group, cyano group, and nitro group, and/or at least one methylene group is substituted with at least one selected from the group consisting of oxygen atom, imino group, sulfonyl group, carbonyl group, arylene group, —C(=O)O—, sulfur atom, and nitroso group. For example, substituted arylene and heteroarylene refer to those obtained by substituting the hydrogen atom of the aryl of arylene and heteroarylene with other group (e.g., halogen). Each $R_2$ may be independently selected from H and C1-C4 alkyl.

The second compound is represented by formula II of wherein each Y is independently selected from carbon and nitrogen, and at least one of Y is nitrogen; each Ar is independently selected from C6-C30 arylene and a single bond, wherein the single bond means that R is directly connected to the benzene ring through the single bond; each R is independently any one selected from the group consisting of halogen, halogen-substituted C1-C6 alkyl, sulfonyl group, carbonyl group, thiol group, cyano group and nitro group, and at least one of R is halogen or halogen-substituted C1-C6 alkyl, wherein C6-C30 arylene is optionally substituted by at least one selected from the group consisting of halogen atom, halogen-substituted C1-C6 alkyl, hydroxyl group, amino group, aryl group, ester group, thiol group, cyano group and nitro group.

At least one Ar may be phenyl or naphthyl, and at least one R may be trifluoromethyl or cyano group.

The co-host material according to one embodiment of the present disclosure comprises the first compound represented by the above formula II.

In the formula II, the plurality of Y are independently selected from carbon and nitrogen (N), and at least one of Y is nitrogen (i.e., not all of Y is carbon).

The plurality of Ar may be independently selected from aryl and a single bond. The single bond can also be understood as the "absence" of Ar group, i.e. the corresponding R group is directly connected to the benzene ring of the second compound main portion by a single bond. In one embodiment, at least one Ar in the second compound is phenyl (i.e., at least one Ar is "present" and is phenyl).

When any one of Ar is phenyl, the corresponding R group may be connected to any position of the phenyl (Ar), namely R and the main portion of the formula may be at any position of the phenyl (Ar), such as ortho-position, para-position, and meta-position; and the attachment position of different R groups to phenyl of each Ar may also be different.

The plurality of R may be independently selected from halogen and halogen substituted C1-C6 alkyl, such as fluorine (F), trifluoromethyl (—CF$_3$), cyano (—CN), and the like; and at least one R is trifluoromethyl or cyano group, and the Ar connected to the R (which is trifluoromethyl or cyano) is phenyl; in other words, in the second compound, at least one trifluoromethyl or cyano group (R) is connected to the benzene ring of the second compound main portion through a phenyl group (Ar). Alternatively, there may also be a fluorine (R) connected to the benzene ring of the second compound main portion through a phenyl group (Ar), or there may also be a trifluoromethyl or a cyano group (R) directly connected to the benzene ring of the second compound main portion (i.e. the corresponding Ar is "absent").

Optionally, the energy levels of the co-host material further satisfy the following requirements:

$|HOMO_1-HOMO_2|>0.3$ eV;

$|LUMO_1-LUMO_2|>0.2$ eV;

$|HOMO_1-LUMO_2|>3.5$ eV, or $|HOMO_2-LUMO_1|>3.5$ eV;

$\Delta Est>0.3$ eV;

$T_{11}>2.65$ eV, and $T_{12}>2.65$ eV;

wherein, | | represents an absolute value, HOMO$_1$ is the highest occupied molecular orbital level of the first compound, HOMO$_2$ is the highest occupied molecular orbital level of the second compound, LUMO$_1$ is the lowest unoccupied molecular orbital level of the first compound, LUMO$_2$ is the lowest unoccupied molecular orbital level of the second compound, $\Delta$ Est is a difference between the triplet excited state energy and the singlet excited state energy of the co-host material, T$_{11}$ is the triplet excited state energy of the first compound, and T$_{12}$ is the triplet excited state energy of the second compound.

In order to ensure that the co-host material is not an exciplex (i.e., the co-host material is a non-exciplex), a part of the energy levels of the first compound, the second compound and the entire co-host material should meet the above requirements.

In addition, from the above definition of the relationship between HOMO and LUMO, it can be known that the minimum energy band gap of one of the co-host materials |HOMO–LUMO|>3.3 eV, and since the co-host material does not produce the exciplex, the co-host material has the energy band gap of at least about 3.3 eV, so it is suitable for more types of thermally activated delayed fluorescent materials.

The co-host material of the present disclosure is prepared as long as the first compound and the second compound are uniformly mixed, specifically, the host material may be obtained by stirring the first compound and the second compound to uniformly mix the same before preparing the light emitting layer; alternatively, the light emitting layer may be prepared directly from the first compound and the second compound by co-evaporation, that is, the co-host material may be prepared simultaneously with the preparation of the light emitting layer.

As can be seen, the co-host material of the present disclosure comprises a P-type host material (the first compound) and an N-type host material (the second compound). For example, the co-host material may be made by mixing the two types of materials. That is, the host material of the present disclosure is a co-host material of a non-exciplex comprising two polar compounds.

The co-host material of the present disclosure is beneficial to the balanced transportation of current carriers, thereby improving the performance of the light emitting device. In addition, the co-host material, which has high T$_1$ (triplet excited state energy) and S$_1$ (singlet excited state energy), facilitates confinement of excitons in an emitter of the TADF material. Moreover, the band gap of the co-host material is wide ($\Delta$ Est>0.3 eV), which is favorable for broadening the selection range of the thermally activated delayed fluorescent material. In addition, since the co-host material is not an exciplex, the emission spectrum of the co-host material does not show obvious red shift, which is favorable for providing a blue light emitting device.

Optionally, in the co-host material, the first compound is present in a mass percentage of 40% to 60%, and the second compound is present in a mass percentage of 40% to 60%.

Optionally, in the co-host material, the first compound is present in a mass percentage of 48% to 52%, and the second compound is present in a mass percentage of 48% to 52%.

In the co-host material of the present disclosure, the contents of the two compounds may be substantially equivalent; for example, the mass percentage of the first compound may be 40% to 60%, and further be 48% to 52%; and the mass percentage of the second compound may be 40% to 60%, and further be 48% to 52%. In some embodiments, the co-host material may consist only of the first compound and the second compound.

Optionally, the first compound comprises at least one of:

(A1)

(A2)

(A3)

, and (A4)

Optionally, the second compound comprises at least one of:

(B1)

(B2)

(B3)

, and (B4)

wherein, the first compound and the second compound are more specifically selected from one of the various substances listed above, and a mixture thereof.

The co-host material according to an embodiment of the present disclosure may be obtained by mixing the above first compound (A3) and the second compound (B3) in equal mass.

Figure 3:
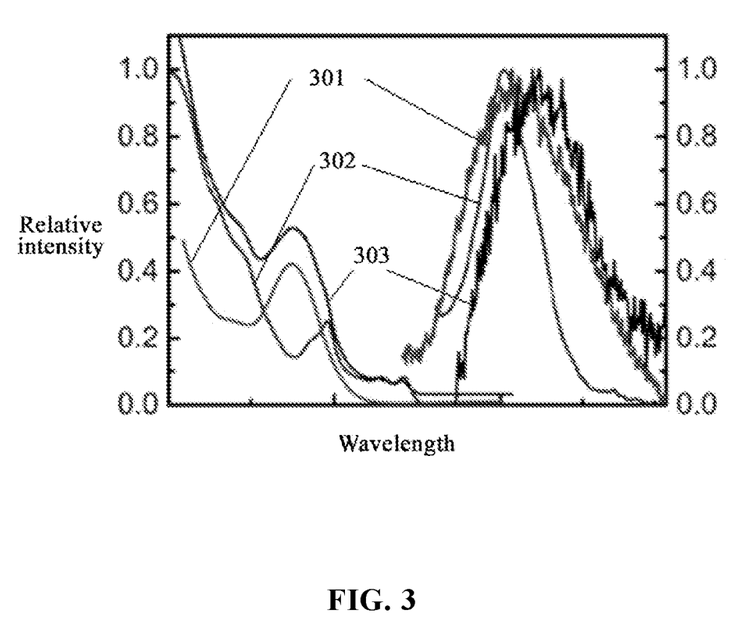
FIG. 3 is an absorption and emission spectrum of the co-host material, the first compound, and the second compound over part of a wavelength range according to one embodiment of the present disclosure.
Figure 4:
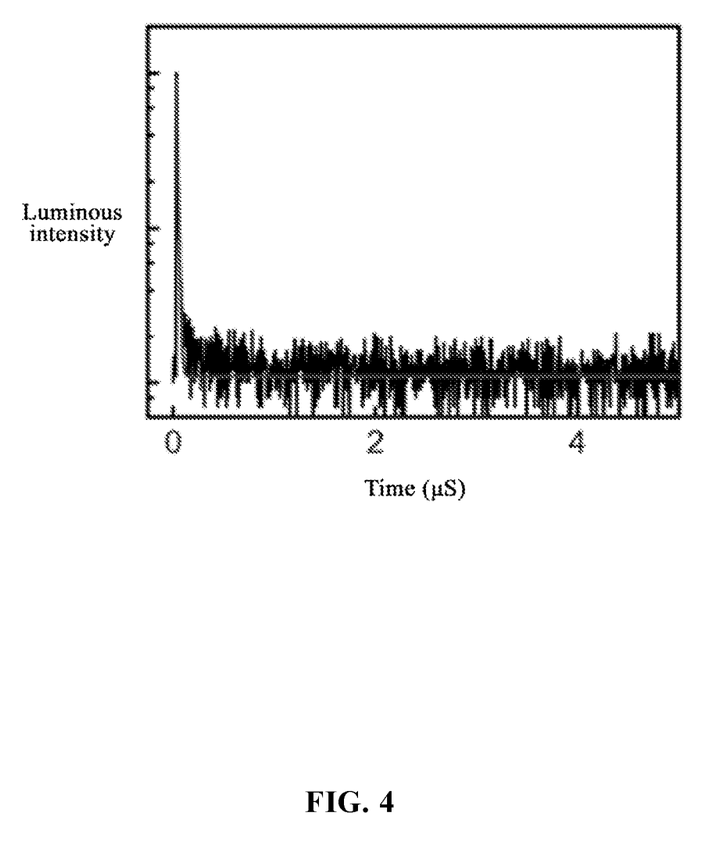
FIG. 4 is a transient fluorescence decay spectrum of the co-host material at room temperature according to one embodiment of the present disclosure.

FIG. 3 shows the absorption and emission spectra of the above co-host material, the first compound and second compound over part of a wavelength range (the absorption spectrum on the left and the emission spectrum on the right). FIG. 4 shows a transient fluorescence decay spectrum of the co-host material at room temperature.

As can be seen from the figures, the co-host material of the present disclosure has good absorption and emission spectra line, and is indeed transiently decayed.

In the second aspect, the present disclosure further provides a composition for forming a light emitting layer, comprising:

the co-host material according to any one described above; and a thermally activated delayed fluorescent material doped in the co-host material.

Specifically, the above co-host material may be mixed with the TADF material to form the material for the light emitting layer of the light emitting device such as an organic light emitting diode.

The composition of the light emitting layer of the present disclosure may be prepared as long as the components of the above co-host material (the first compound and the second compound) and the thermally activated delayed fluorescent dopant material are uniformly mixed, and specifically, the first compound, the second compound and the thermally activated delayed fluorescent dopant material may directly be mixed uniformly by stirring before preparing the light emitting layer; alternatively, two of the first compound, the second compound and the thermally activated delayed fluorescent dopant material may be uniformly mixed to obtain a mixture, and then the mixture is uniformly mixed with the rest one; alternatively, the light emitting layer may be prepared from the first compound, the second compound, and the thermally activated delayed fluorescent dopant material by co-evaporation, that is, the light emitting layer material may be prepared simultaneously with the preparation of the light emitting layer.

Optionally, in the composition, the thermally activated delayed fluorescent dopant material may be present in a mass percentage of 0.5% to 40%; and the co-host material may be present in a mass percentage of 60% to 99.5%.

Optionally, in the composition, the thermally activated delayed fluorescent dopant material may be present in a mass percentage of 1% to 10%; and the co-host material may be present in a mass percentage of 90% to 99%.

In the above composition for forming the light emitting layer, the thermally activated delayed fluorescent material is a dopant, and thus its content should not be too high. The mass percentage of the thermally activated delayed fluorescent material may be 0.5% to 40%, further be 1% to 10%, and more further be 1% to 3%; and the mass percentage of the co-host material may be 60% to 99.5%, further be 90% to 99%, and more further be 97% to 99%. In some embodiments, the light emitting layer material may consist only of the co-host material and the thermally activated delayed fluorescent dopant material.

The thermally activated delayed fluorescent material may be known in the art, and for example, it may comprise at least one of a backbone polymeric thermally activated delayed fluorescent polymer, a side chain thermally activated delayed fluorescent polymer, and a dendritic thermally activated delayed fluorescent compound.

Figure 1:
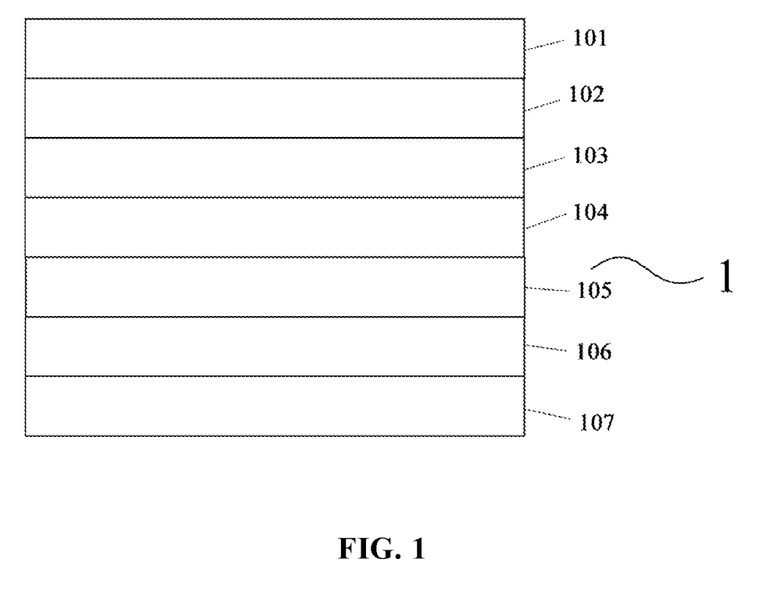
FIG. 1 a schematic cross-sectional structure of the light emitting device according to one embodiment of the present disclosure.

Optionally, the thermally activated delayed fluorescent material comprises the compounds of:

Referring to FIG. 1, in the third aspect, the present disclosure further provides a light emitting device 1 comprising:

the light emitting layer EL formed from any one of the above compositions; and the anode and the cathode disposed on two sides of the light emitting layer EL respectively.

Referring to FIG. 1, the above light emitting layer composition (the co-host material and the thermally activated delayed fluorescent dopant material) may be uniformly mixed to form the light emitting layer EL, and combined with the Anode, the Cathode, and the like, so as to obtain the light emitting device 1 with light emitting functions.

The light emitting device 1 may specifically be an OLED.

Optionally, the light emitting device 1 further comprises:

the hole injection layer 106 disposed between the anode 107 and the light emitting layer 104;

the hole transport layer 105 disposed between the hole injection layer 106 and the light emitting layer 104;

the electron injection layer 102 disposed between the cathode 101 and the light emitting layer 104; and the electron transport layer 103 disposed between the electron injection layer 102 and the light emitting layer 104.

Referring to FIG. 1, in order to improve the performance of the light emitting device 1, the light emitting device 1 may have a plurality of auxiliary layers in addition to the light emitting layer 104, the cathode 101, and the anode 107.

The light emitting device 1 may further comprise other auxiliary layers (not shown) such as a hole blocking layer (HBL) and an electron blocking layer (EBL) (not shown in Figures).

The light emitting device 1 may have all or only a part of the above auxiliary layers.

Each auxiliary layer may be a single-layer structure, or a laminated structure composed of a plurality of sub-layers.

Optionally, the light emitting layer 104 has a thickness of 10 nm to 100 nm.

When the co-host material of the present disclosure is adopted, the thickness of the corresponding light emitting layer EL may be 10 nm to 100 nm.

Optionally, the light emitting device 1 is a green light emitting device, a red light emitting device, or a blue light emitting device.

As described above, since the co-host material of the present disclosure is used in the light emitting layer 104 of the light emitting device 1, the light emitted from the light emitting layer EL is not red-shifted and of low difficulty in emitting blue light, so that the light emitting device 1 of the present disclosure may be specifically used for a blue light emitting device for emitting blue light.

Alternatively, the co-host material of the present disclosure may also be used for light emitting devices of other colors, such as red light emitting devices, green light emitting devices, and yellow light emitting devices.

In the fourth aspect, the present disclosure further provides a display substrate, comprising:

a base; and a plurality of light emitting devices disposed on the base, wherein at least a portion of the light emitting devices are any one of the light emitting devices described above.

The plurality of light emitting devices (e.g., organic light emitting diodes) may be fabricated on the base, with each light emitting device being a sub-pixel to obtain a display substrate (e.g., an organic light emitting diode display substrate) for displaying.

The display substrate may have another structure. For example, the display substrate may comprise gate lines, data lines, control electrode lines, etc. for controlling signals written to the sub-pixels, pixel circuits for driving the corresponding light emitting devices to emit light in each sub-pixel and the like.

Figure 2:
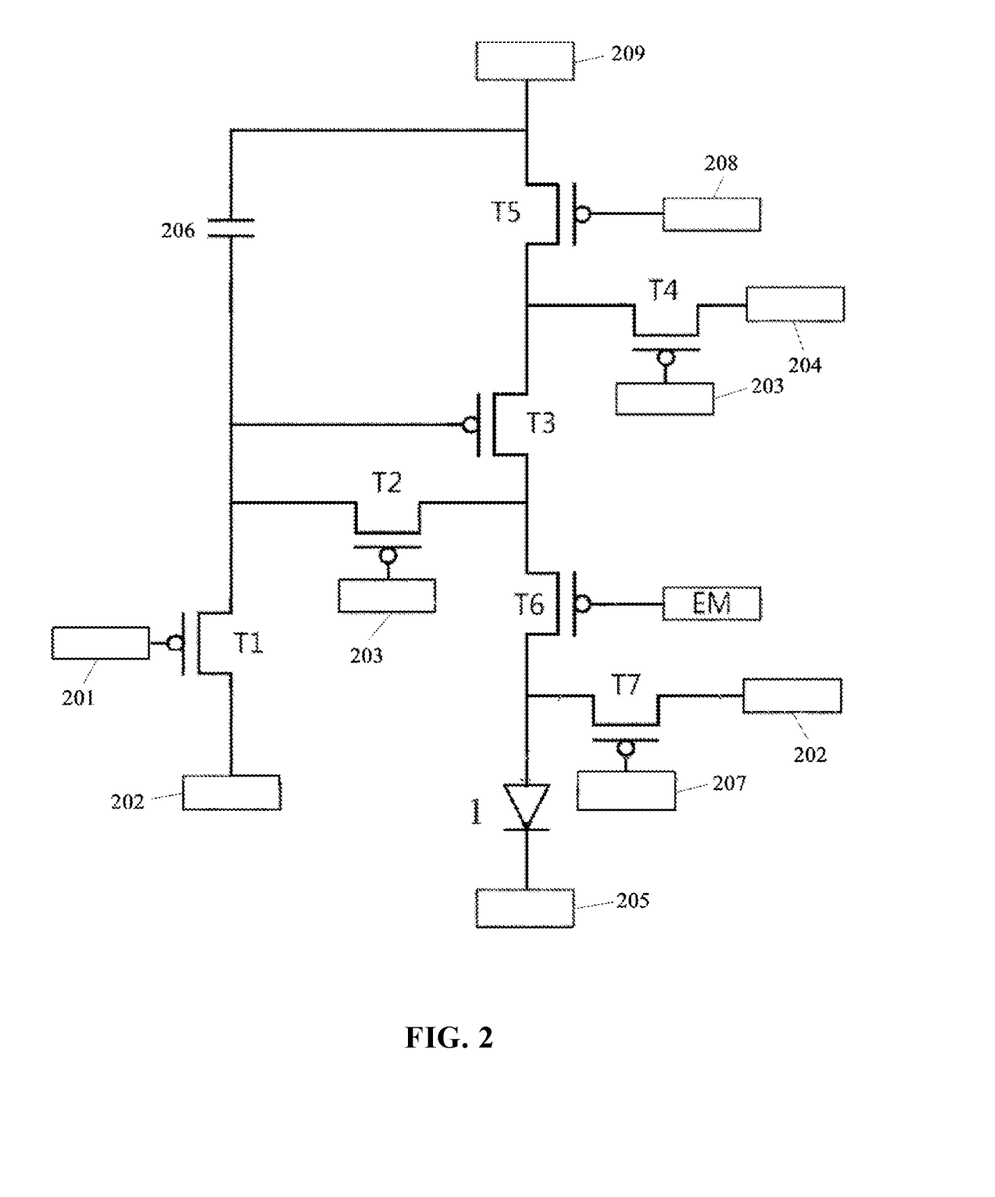
FIG. 2 is a schematic circuit diagram of a pixel circuit in the display substrate according to one embodiment of the present disclosure.

For example, referring to FIG. 2, the structure of a usable pixel circuit is 7T1C structure, which comprises the first transistor T1, the second transistor T2, the third transistor T3, the fourth transistor T4, the fifth transistor T5, the sixth transistor T6, the seventh transistor T7, the storage capacitor 206, the light emitting device 1, the first reset terminal 201, the second reset terminal 207, the initialized terminal 202, the gate line terminal 203, the data line terminal 204, the control line terminal 208, the positive electrode terminal 209, the negative electrode terminal 205, etc.

In the fifth aspect, the present disclosure further provides a display device comprising the display substrate described above.

The display device with display function can be obtained by combining the display substrate with other devices (such as a pair of box substrates, a frame, a shell, a driving chip, and a power supply).

Specifically, the display device may be any product or component having a display function, such as an OLED display panel, an electronic paper, a mobile phone, a tablet computer, a television, a display, a notebook computer, a digital photo frame, and a navigator.

EXAMPLES

Hereinafter, some organic light emitting diodes (light emitting devices) were prepared using the co-host material of the present disclosure and other host materials, as examples and comparative examples, wherein the following raw material compounds were used:

Compound 1 is $ReO_3$ (rhenium trioxide);

Compound 2 (the first compound) has a structural formula of:

Compound 3 (the second compound) has a structural formula of:

Compound 4 (the thermally activated delayed fluorescent dopant material) has a structural formula of:

Compound 5 (the second compound) has a structural formula of:

Compound 6 (the first compound) has a structural formula of:

Compound 7 (the second compound) has a structural formula of:

Example 1

This example prepares an organic light emitting diode (light emitting device) comprising steps of:
S1, vacuum-evaporating an indium tin oxide (ITO) anode with a film thickness of 100 nm on a glass substrate by vacuum evaporation under the environment of a vacuum degree of $1 \times 10^{-5}$ Pa;
S2, co-evaporating compound 1 and compound 2 on the substrate to form a hole injection layer with a film thickness of 60 nm, wherein the compound 1 has a mass percentage of 4%, and the compound 2 has a mass percentage of 96%;
S3, evaporating compound 2 on the hole injection layer to form a hole transport layer with a film thickness of 15 nm;
S4, co-evaporating compound 2, compound 3 and compound 4 on the hole transport layer to form a light emitting layer with a film thickness of 20 nm, wherein the compound 2 has a mass percentage of 50%, compound 3 has a mass percentage of 49% (namely the co-host material is a mixture of the compound 2 and the compound 3), and the compound 4 has a mass percentage of 1%; the HOMO energy level is measured by AC2; the LUMO energy level is calculated according to the measured HOMO energy level and the UV absorption spectrum of the material; the T11 and T12 of the host material are obtained by the low-temperature phosphorescence emission spectrum test; as a result, the energy level relations of the made host material are as follows: $|HOMO_1-HOMO_2|>0.3$ eV; $|LUMO_1-LUMO_2|>0.2$ eV; $|HOMO_1-LUMO_2|>3.5$ eV; $\Delta Est>0.3$ eV; $T_{11}>2.65$ eV, and $T_{12}>2.65$ eV;
S5, evaporating the compound 3 on the light emitting layer to form a first sub electron transport layer (ETL-1) with a film thickness of 10 nm; and evaporating compound 5 on the first sub electron transport layer to form a second sub electron transport layer (ETL-2) with a film thickness of 40 nm;
S6, evaporating lithium fluoride (LiF) on the second sub electron transport layer to form an electron injection layer with a film thickness of 1 nm; and
S7, evaporating aluminum (Al) on the electron injection layer to form a cathode with a film thickness of 80 nm, thereby obtaining the organic light emitting diode of Example 1.

Comparative Example 1

This example prepares an organic light emitting diode (light emitting device) comprising steps of:
S1, vacuum-evaporating an indium tin oxide (ITO) anode with a film thickness of 100 nm on a glass substrate by vacuum evaporation under the environment of a vacuum degree of $1 \times 10^{-5}$ Pa;
S2, co-evaporating compound 1 and compound 2 on the substrate to form a hole injection layer with a film thickness of 60 nm, wherein the compound 1 has a mass percentage of 4%, and the compound 2 has a mass percentage of 96%;
S3, evaporating the compound 2 on the hole injection layer to form a hole transport layer with a film thickness of 15 nm;
S4, co-evaporating the compound 2 and compound 4 on the hole transport layer to form a light emitting layer with a film thickness of 20 nm, wherein the compound 2 has a mass percentage of 99% (namely the host material comprises only compound 2), and the compound 4 has a mass percentage of 1%;

S5, evaporating compound 3 on the light emitting layer to form a first sub electron transport layer with a film thickness of 10 nm; and evaporating compound 5 on the first sub electron transport layer to form a second sub electron transport layer with a film thickness of 40 nm;

S6, evaporating lithium fluoride (LiF) on the second sub electron transport layer to form an electron injection layer with a film thickness of 1 nm; and S7, evaporating aluminum (Al) on the electron injection layer to form a cathode with a film thickness of 80 nm, thereby obtaining the organic light emitting diode of Comparative Example 1.

Comparative Example 2

This example prepares an organic light emitting diode (light emitting device) comprising steps of:

S1, vacuum-evaporating an indium tin oxide (ITO) anode with a film thickness of 100 nm on a glass substrate by vacuum evaporation under the environment of a vacuum degree of $1 \times 10^{-5}$ Pa;

S2, co-evaporating compound 1 and compound 2 on the substrate to form a hole injection layer with a film thickness of 60 nm, wherein the compound 1 has a mass percentage of 4%, and the compound 2 has a mass percentage of 96%;

S3, evaporating compound 2 on the hole injection layer to form a hole transport layer with a film thickness of 15 nm;

S4, co-evaporating compound 3 and compound 4 on the hole transport layer to form a light emitting layer with a film thickness of 20 nm, wherein the compound 3 has a mass percentage of 99% (namely the host material comprises only compound 3), and the compound 4 has a mass percentage of 1%;

S5, evaporating compound 3 on the light emitting layer to form a first sub electron transport layer with a film thickness of 10 nm; and evaporating compound 5 on the first sub electron transport layer to form a second sub electron transport layer with a film thickness of 40 nm;

S6, evaporating lithium fluoride (LiF) on the second sub electron transport layer to form an electron injection layer with a film thickness of 1 nm; and S7, evaporating aluminum (Al) on the electron injection layer to form a cathode with a film thickness of 80 nm, thereby obtaining the organic light emitting diode of Comparative Example 2.

Example 2

This example prepares an organic light emitting diode (light emitting device) comprising steps of:

S1, vacuum-evaporating an indium tin oxide (ITO) anode with a film thickness of 100 nm on a glass substrate by vacuum evaporation under the environment of a vacuum degree of $1 \times 10^{-5}$ Pa;

S2, co-evaporating compound 1 and compound 6 on the substrate to form a hole injection layer with a film thickness of 60 nm, wherein the compound 1 has a mass percentage of 4%, and the compound 6 has a mass percentage of 96%;

S3, evaporating compound 6 on the hole injection layer to form a hole transport layer with a film thickness of 15 nm;

S4, co-evaporating compound 6, compound 7 and compound 4 on the hole transport layer to form a light emitting layer with a film thickness of 20 nm, wherein the compound 6 has a mass percentage of 50%, the compound 7 has a mass percentage of 49% (namely the co-host material is a mixture of compound 6 and compound 7), and the compound 4 has a mass percentage of 1%, and the HOMO energy level is measured by AC2; the LUMO energy level is calculated according to the measured HOMO energy level and the UV absorption spectrum of the material; the T11 and T12 of the host material are obtained by the low-temperature phosphorescence emission spectrum test; as a result, the energy level relations of the made host material are as follows: $|HOMO_1-HOMO_2|>0.3$ eV; $|LUMO_1-LUMO_2|>0.2$ eV; $|HOMO_1-LUMO_2|>3.5$ eV; $\Delta Est>0.3$ eV; $T_{11}>2.65$ eV, and $T_{12}>2.65$ eV;

S5, evaporating compound 3 on the light emitting layer to form a first sub electron transport layer with a film thickness of 10 nm; and evaporating compound 5 on the first sub electron transport layer to form a second sub electron transport layer with a film thickness of 40 nm;

S6, evaporating lithium fluoride (LiF) on the second sub electron transport layer to form an electron injection layer with a film thickness of 1 nm; and S7, evaporating aluminum (Al) on the electron injection layer to form a cathode with a film thickness of 80 nm, thereby obtaining the organic light emitting diode of Example 2.

The OLEDs of the above Examples and Comparative Examples were tested for the main emission wavelength and the external quantum efficiency (EQE), and the results are shown in Table 1:

TABLE 1

Performance of organic light emitting diodes of Examples and Comparative Examples

| Host material | Main emission wavelength (nm) | External quantum efficiency (%) |
| --- | --- | --- |
| Compound 2:Compound 3 (Example 1) | 500 | 24.8 |
| Compound 6:Compound 7 (Example 2) | 498 | 25.2 |
| Compound 2 Comparative Example 1 | 503 | 20.1 |
| Compound 3 Comparative Example 2 | 502 | 9.5 |

As can be seen from Table 1, the external quantum efficiency of the organic light emitting diode (of each Example) using the co-host material (a mixture of the first compound and the second compound) of the embodiments of the present disclosure is significantly higher than the external quantum efficiency of the organic light emitting diode (of each Comparative Example) using a single substance (the first compound or the second compound) as the host material. This indicates that the co-host material of the embodiments of the present disclosure can significantly improve the performance of the organic light emitting diode.

In addition, the additive external quantum efficiency of the compound 2 and compound 3 in a ratio of 50:50 is 15.25%, which is significantly less than the actually tested quantum efficiency of Example 1. Therefore, the co-host material formed from the first compound and the second compound further provides a synergistic effect in improving the performance of the organic light emitting diode.

Finally, as can be seen from Table 1, the Examples 1 and 2 do not show a significant red shift and thus can provide the light emitting layer of the blue light emitting device.

It can be understood that the foregoing embodiments are merely illustrative embodiments employed for describing the principle of the present disclosure. However, the present disclosure is not limited thereto. For a skilled person in the art, various variations and modifications can be made without departing from the spirit and essence of the present disclosure. These variations and modifications are regarded as the protection scope of the present disclosure.

The invention claimed is:

1. A co-host material comprising:
a first compound represented by formula I of wherein X is selected from carbon and silicon; each $R_1$ is independently selected from any of hydrogen, carbazole, dibenzocarbazole, dibenzofuran and dibenzothiophene, and at least one of $R_1$ is carbazole connected to a benzene ring through a nitrogen atom in the carbazole; each $R_2$ is independently selected from the group consisting of hydrogen, substituted or unsubstituted C1-C12 alkyl, substituted or unsubstituted C6-C30 arylene, and substituted or unsubstituted C3-C30 heteroarylene; and in the case of substitution, at least one hydrogen of the C1-C12 alkyl, the C6-C30 arylene, and the C3-C30 heteroarylene is substituted with at least one selected from the group consisting of halogen atom, hydroxyl group, amino group, aryl group, ester group, thiol group, cyano group, and nitro group, and/or at least one methylene is substituted with at least one selected from the group consisting of oxygen atom, imino group, sulfone group, carbonyl group, arylene, —C(=O)O—, sulfur atom, and nitroso group; and a second compound represented by formula II of wherein each Y is independently selected from carbon and nitrogen, and at least one of Y is nitrogen; each Ar is independently selected from C6-C30 arylene and a single bond, wherein the single bond means that R is directly connected to a benzene ring through the single bond; each R is independently selected from at least one in the group consisting of halogen, halogen-substituted C1-C6 alkyl, sulfonyl group, carbonyl group, thiol group, cyano group and nitro group, and at least one of R is halogen or halogen-substituted C1-C6 alkyl, wherein C6-C30 arylene is optionally substituted by at least one selected from the group consisting of halogen atom, halogen-substituted C1-C6 alkyl, hydroxyl group, amino group, aryl group, ester group, thiol group, cyano group and nitro group.

2. The co-host material of claim 1, wherein at least one of Ar is phenyl or naphthyl, and at least one of R is trifluoromethyl or cyano group.

3. The co-host material of claim 1, wherein each $R_2$ is independently selected from H or C1-C4 alkyl.

4. The co-host material of claim 1, wherein the co-host material satisfies energy level relationship of:

$|HOMO_1 - HOMO_2| > 0.3$ eV;

$|LUMO_1 - LUMO_2| > 0.2$ eV;

$|HOMO_1 - LUMO_2| > 3.5$ eV, or $|HOMO_2 - LUMO_1| > 3.5$ eV;

$\Delta Est > 0.3$ eV;

$T_{11} > 2.65$ eV, and $T_{12} > 2.65$ eV;

wherein, | | represents an absolute value, $HOMO_1$ is the highest occupied molecular orbital level of the first compound, $HOMO_2$ is the highest occupied molecular orbital level of the second compound, $LUMO_1$ is the lowest unoccupied molecular orbital level of the first compound, $LUMO_2$ is the lowest unoccupied molecular orbital level of the second compound, $\Delta$ Est is a difference between the triplet excited state energy and the singlet excited state energy of the co-host material, $T_{11}$ is the triplet excited state energy of the first compound, and $T_{12}$ is the triplet excited state energy of the second compound.

5. The co-host material of claim 1, wherein
in the co-host material, the first compound is present in a mass percentage of 40% to 60%, and the second compound is present in a mass percentage of 40% to 60%.

6. The co-host material of claim 1, wherein
in the co-host material, the first compound is present in a mass percentage of 48% to 52%, and the second compound is present in a mass percentage of 48% to 52%.

7. The co-host material of claim 1, wherein the first compound is at least one selected from in the group consisting of:

,

, and

.

8. The co-host material of claim 1, wherein the second compound is at least one selected from in the group consisting of:

,

9. The co-host material of claim 1, wherein the co-host material is not an exciplex.

10. A composition for forming a light emitting layer, comprising:
    the co-host material according to claim 1; and
    a thermally activated delayed fluorescent material doped in the co-host material.

11. The composition of claim 10, wherein
    in the composition, the thermally activated delayed fluorescent material is present in a mass percentage of 0.5% to 40%; and the co-host material is present in a mass percentage of 60% to 99.5%.

12. The composition of claim 10, wherein
    in the composition, the thermally activated delayed fluorescent material is present in mass percentage of 1% to 10%; and the co-host material 1 is present in a mass percentage of 90% to 99%.

13. The composition of claim 10, wherein the thermally activated delayed fluorescent material is at least one selected from the group consisting of a backbone polymeric thermally activated delayed fluorescent polymer, a side chain thermally activated delayed fluorescent polymer, and a dendritic thermally activated delayed fluorescent compound.

14. The composition of claim 10, wherein the thermally activated delayed fluorescent material comprises compound of:

15. The composition of claim 10, wherein the co-host material is not an exciplex.

16. A light emitting device, comprising:
    a light emitting layer formed from the composition of claim 10; and
    an anode and a cathode disposed on two sides of the light emitting layer respectively.

17. The light emitting device of claim 16, further comprising:
    a hole injection layer disposed between the anode and the light emitting layer;
    a hole transport layer disposed between the hole injection layer and the light emitting layer;
    an electron injection layer disposed between the cathode and the light emitting layer; and
    an electron transport layer disposed between the electron injection layer and the light emitting layer.

18. The light emitting device of claim 16, wherein the light emitting layer has a thickness of 10 nm to 100 nm.

19. The light emitting device of claim 16, wherein the light emitting device is a red light emitting device, a green light emitting device or a blue light emitting device.

20. The light emitting device of claim 16, wherein the thermally activated delayed fluorescent material comprises compound of:

* * * * *